United States Patent
Handa et al.

(10) Patent No.: US 7,737,231 B2
(45) Date of Patent: Jun. 15, 2010

(54) PROCESS FOR PRODUCING WATER-ABSORBING RESIN

(75) Inventors: Masayoshi Handa, Himeji (JP); Takayasu Taniguchi, Himeji (JP); Yasuhiro Nawata, Himeji (JP); Masato Fujikake, Himeji (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 159 days.

(21) Appl. No.: 10/501,507

(22) PCT Filed: Dec. 27, 2002

(86) PCT No.: PCT/JP02/13769

§ 371 (c)(1), (2), (4) Date: Jul. 15, 2004

(87) PCT Pub. No.: WO03/059962

PCT Pub. Date: Jul. 24, 2003

(65) Prior Publication Data

US 2005/0085604 A1  Apr. 21, 2005

(30) Foreign Application Priority Data

Jan. 16, 2002 (JP) ............................. 2002-007813

(51) Int. Cl.
C08F 2/18 (2006.01)
C08F 4/28 (2006.01)

(52) U.S. Cl. ........................ 526/78; 526/227; 526/317.1

(58) Field of Classification Search ................... 526/78, 526/227, 317.1; 442/381
See application file for complete search history.

(56) References Cited

U.S. PATENT DOCUMENTS

| 4,397,776 | A | * | 8/1983 | Ward ............................ 510/407 |
| 4,959,060 | A | * | 9/1990 | Shimomura et al. ......... 604/368 |
| 5,041,508 | A | * | 8/1991 | Haruna et al. ................ 526/204 |
| 5,194,550 | A | * | 3/1993 | Rance et al. ............ 526/318.25 |
| 5,773,542 | A | * | 6/1998 | Koudate et al. .............. 526/215 |
| 5,814,304 | A | * | 9/1998 | Wong et al. .................... 424/53 |
| 6,300,306 | B1 | * | 10/2001 | Firkins et al. ............... 510/476 |
| 6,313,231 | B1 | * | 11/2001 | Hosokawa et al. ........... 525/340 |
| 6,797,656 | B2 | * | 9/2004 | Tsuchiya et al. ............. 442/417 |
| 2001/0021375 | A1 | * | 9/2001 | Hossel et al. .................. 424/59 |
| 2002/0034911 | A1 | * | 3/2002 | Tsuchiya et al. ............. 442/381 |
| 2004/0110914 | A1 | * | 6/2004 | Nakahara et al. .......... 526/317.1 |
| 2004/0247871 | A1 | * | 12/2004 | Tsuchiya et al. ........ 428/402.21 |
| 2005/0085604 | A1 | * | 4/2005 | Handa et al. ................. 526/227 |

FOREIGN PATENT DOCUMENTS

| CN | 1300803 A |   | 6/2001 |
| EP | 0 257 951 | * | 2/1988 |
| EP | 889063 A1 | * | 1/1999 |
| EP | 889063 A1 |   | 1/1999 |
| EP | 1 034 801 A1 |   | 9/2000 |
| EP | 1142696 A1 |   | 10/2001 |
| JP | 63146964 A | * | 6/1988 |
| JP | 05-086251 |   | 4/1993 |
| JP | 05-086251 A |   | 4/1993 |
| JP | 05086251 A | * | 4/1993 |
| JP | 2927871 |   | 7/1999 |
| JP | 11-322846 |   | 11/1999 |
| JP | 2000-230129 A |   | 8/2000 |
| JP | 2000230129 A | * | 8/2000 |
| JP | 2000-327926 A |   | 11/2000 |
| JP | 2000327926 A | * | 11/2000 |
| JP | 2003-052742 |   | 2/2003 |
| WO | WO 94/20547 |   | 9/1994 |
| WO | WO 00/55245 |   | 9/2000 |

OTHER PUBLICATIONS

"Versenex 80 Chelating Agent", Dow Chemical Company Technical Data, Jun. 2002, pp. 1-2.

* cited by examiner

*Primary Examiner*—David Wu
*Assistant Examiner*—Michael M Bernshteyn
(74) *Attorney, Agent, or Firm*—Birch, Stewart, Kolasch & Birch, LLP

(57) ABSTRACT

A process for preparing a water-absorbent resin made from an $\alpha,\beta$-unsaturated carboxylic acid as an essential monomer characterized in that the process comprises allowing a metal chelating agent to be present at any step in the process in an amount of 0.001 to 6 parts by weight, based on 100 parts by weight of the $\alpha,\beta$-unsaturated carboxylic acid; and adding a reducing agent or an oxidizing agent thereto in an amount of 0.001 to 6 parts by weight, based on 100 parts by weight of the $\alpha,\beta$-unsaturated carboxylic acid before initiation of drying and/or during drying of a gelated product containing a water-absorbent resin obtained by polymerization.

10 Claims, No Drawings

PROCESS FOR PRODUCING WATER-ABSORBING RESIN

TECHNICAL FIELD

The present invention relates to a process for preparing a water-absorbent resin. More specifically, the present invention relates to a process for preparing a water-absorbent resin having no discoloration immediately after the preparation, and having excellent discoloration resistance, which can be suitably used as an absorbent article of hygienic materials such as paper diapers and sanitary napkins.

BACKGROUND ART

Water-absorbent resins have been widely used as absorbent articles for hygienic materials such as paper diapers and sanitary napkins, utilizing the feature that a water-based liquid, for instance, a body fluid such as human urine, blood or sweat is quickly absorbed in a large amount, so that the liquid once absorbed is not released even under a load.

Conventional water-absorbent resins have some problems that the water-absorbent resins discolor into yellow even immediately after the preparation depending upon the preparation processes, or that the resins are likely to discolor into yellow, brown or the like by an external factor such as heat or humidity when the resins are allowed to stand even if the resins are white immediately after the preparation. In the field of the above-mentioned hygienic materials such as paper diapers, when a water-absorbent resin discolors in the absorbent article, the commercial value as an absorbent article is drastically lowered. Therefore, under severe high-temperature, high-humidity environment such as storehouse in the summer time, it has been desired that a water-absorbent resin does not discolor when the water-absorbent resin or absorbent article is subjected to storage for a long period of time.

As water-absorbent resins having an effect of preventing discoloration, there have been known, for instance, a high water-absorbent polymer composition in which an organic phosphoric acid compound or a salt thereof is added to a high water-absorbent polymer (Japanese Patent Laid-Open No. Hei 5-86251); an absorbent composition comprising an acidic water-swellable crosslinked polymer, a basic water-swellable crosslinked polymer, a discoloration preventive and/or an antioxidant and/or a boron-containing compound (Japanese Patent Laid-Open No. 2000-230129); an absorbent composition comprising a water-absorbent resin, and an organic carboxylic acid and/or a salt thereof (Japanese Patent Laid-Open No. 2000-327926) and the like. However, the above compositions do not exhibit a sufficiently satisfactory effect of preventing discoloration when subjected to high-temperature, high-humidity storage for a long period of time.

Accordingly, an object of the present invention is to provide a water-absorbent resin having no discoloration immediately after the preparation, and having suppressed discoloration even when subjected to a room temperature storage or even to a high-temperature, high-humidity storage for a long period of time.

These and other objects of the present invention will be apparent from the following description.

DISCLOSURE OF INVENTION

Concretely, the present invention relates to:
[1] a process for preparing a water-absorbent resin made from an α,β-unsaturated carboxylic acid as an essential monomer characterized in that the process comprises allowing a metal chelating agent to be present at any step in the process in an amount of 0.001 to 6 parts by weight, based on 100 parts by weight of the α,β-unsaturated carboxylic acid; and adding a reducing agent or an oxidizing agent thereto in an amount of 0.001 to 6 parts by weight, based on 100 parts by weight of the α,β-unsaturated carboxylic acid before initiation of drying and/or during drying of a gelated product containing a water-absorbent resin obtained by polymerization;
[2] a water-absorbent resin obtainable by the process of the above [1], wherein the water-absorbent resin has Yellow Index of 12 or less, after allowing to stand at 50° C. and 90% relative humidity for 20 days;
[3] an absorbent comprising a water-absorbent resin obtained by the process of the above [1], and a hydrophilic fiber;
[4] an absorbent article comprising the absorbent of the above [3], wherein the absorbent is kept between a liquid-permeable sheet and a liquid-impermeable sheet; and
[5] a method for preventing discoloration of a water-absorbent resin made from an α,β-unsaturated carboxylic acid as an essential monomer, wherein the method comprises preparing the water-absorbent resin by a process comprising allowing a metal chelating agent to be present at any stage in the process in an amount of 0.001 to 6 parts by weight, based on 100 parts by weight of the α,β-unsaturated carboxylic acid; and adding a reducing agent or an oxidizing agent thereto in an amount of 0.001 to 6 parts by weight, based on 100 parts by weight of the α,β-unsaturated carboxylic acid before initiation of drying and/or during drying of a gelated product containing a water-absorbent resin obtained by polymerization.

BEST MODE FOR CARRYING OUT THE INVENTION

The process for preparing a water-absorbent resin of the present invention has a feature in that a water-absorbent resin having no discoloration immediately after the preparation, and having suppressed discoloration even when subjected to a room temperature storage or even to a high-temperature, high-humidity storage for a long period of time can be prepared by a process comprising allowing a metal chelating agent to be present at any step in the process in an amount of 0.001 to 6 parts by weight, based on 100 parts by weight of the α,β-unsaturated carboxylic acid; and adding a reducing agent or an oxidizing agent thereto in an amount of 0.001 to 6 parts by weight, based on 100 parts by weight of the α,β-unsaturated carboxylic acid before initiation of drying and/or during drying of a gelated product containing a water-absorbent resin obtained by polymerization.

As the polymerization method for the water-absorbent resin, representative preparation processes such as reversed phase suspension polymerization method and aqueous solution polymerization method are usable without being limited thereto. The water-absorbent resin can be prepared by drying the water-absorbent resin obtained by the above-mentioned polymerization method, and removing water and an organic solvent.

At any step of preparing a water-absorbent resin, the method of allowing a metal chelating agent to be present includes (i) a method of adding the above-mentioned chelating agent to an aqueous solution of the monomer comprising an α,β-unsaturated carboxylic acid before the polymerization; (ii) a method of adding the above-mentioned chelating agent to a water-containing gelated product after the polymerization; (iii) a method of adding the above-mentioned chelating agent to a water-absorbent resin during drying; (iv)

a method of powder-blending the above-mentioned chelating agent with a water-absorbent resin after drying; (v) a method of adding the above-mentioned chelating agent to a water-absorbent resin dispersed in an organic solvent, and heating and removing the solvent from the mixture; and the like.

It is preferable that the embodiment of adding a metal chelating agent is, but not particularly limited to, an embodiment of adding a solution prepared by dissolving a liquid or powder metal chelating agent in a hydrophilic solvent such as water, or an embodiment of adding a fine powder of a metal chelating agent in a powdery state, in order that the metal chelating agent is homogeneously dispersed in the water-absorbent resin. Here, the particle size of the fine metal chelating agent powder is not particularly limited. It is preferable that 80% by weight of the entire particles have particle sizes of 100 μm or less, from the viewpoint that a satisfactory effect of preventing discoloration is obtained when the amount of coarse grain portions is smaller.

The metal chelating agent usable in the present invention includes phosphoric acid-based metal chelating agents such as pyrophosphoric acid and tripolyphosphoric acid, and salts thereof; carboxylic acid-based metal chelating agents such as citric acid, tartaric acid and phthalic acid, and salts thereof; aminocarboxylic acid-based metal chelating agents such as iminodiacetic acid, hydroxyethyliminodiacetic acid, nitrilotriacetic acid, nitrilotripropionic acid, ethylenediaminetetraacetic acid, diethylenetriaminepentaacetic acid, triethylenetetraminehexaacetic acid, trans-1,2-diaminocyclohexanetetraacetic acid, N,N-bis(2-hydroxyethyl)glycine, diaminopropanoltetraacetic acid, ethylenediaminedipropionic acid, hydroxyethylenediaminetriacetic acid, glycol ether diaminetetraacetic acid, diaminopropanetetraacetic acid, N,N'-bis(2-hydroxybenzyl)ethylenediamine-N,N'-diacetic acid, and 1,6-hexamethylenediamine-N,N,N',N'-tetraacetic acid, and salts thereof; and the like. Among them, phosphoric acid-based metal chelating agents, aminocarboxylic acid-based metal chelating agents and salts thereof are preferably used, from the viewpoint of the effect of preventing discoloration. Especially, diethylenetriaminepentaacetic acid, triethylenetetraminehexaacetic acid, trans-1,2-diaminocyclohexanetetraacetic acid, ethylenediaminetetraacetic acid, tripolyphosphoric acid, and salts thereof are more preferably used.

The amount of the above-mentioned metal chelating agent used is from 0.001 to 6 parts by weight, preferably from 0.005 to 3 parts by weight, more preferably from 0.01 to 2 parts by weight, based on 100 parts by weight of the α,β-unsaturated carboxylic acid. When the amount of the metal chelating agent used is 0.001 parts by weight or more, a satisfactory effect for preventing discoloration can be obtained. Also, when the amount of the metal chelating agent used is 6 parts by weight or less, the effect corresponding to the amount used is obtained, and is economically advantageous.

It is preferable that the method of adding a reducing agent or an oxidizing agent is a method of adding the reducing agent or the oxidizing agent before initiation of drying and/or during drying of a gelated product containing a water-absorbent resin obtained by the polymerization, from the viewpoint that the procedures in the preparation steps are simplified.

It is preferable that the embodiment of adding the reducing agent or the oxidizing agent mentioned above is, but not particularly limited to, an embodiment of adding a solution prepared by dissolving a liquid or powder of a reducing agent or an oxidizing agent in a hydrophilic solvent such as water, or an embodiment of adding a fine powder of a reducing agent or an oxidizing agent in a powdery state, in order that the reducing agent or the oxidizing agent is homogeneously dispersed in the water-absorbent resin.

In addition, the order of addition of the metal chelating agent and the reducing agent or the oxidizing agent is not particularly limited. Either one can be added first, or they may be added simultaneously. A method of adding a reducing agent or an oxidizing agent and thereafter adding a metal chelating agent is more preferable from the aspect of the effect of preventing discoloration.

The reducing agent usable in the present invention includes sulfites such as sodium sulfite, potassium sulfite, calcium sulfite, zinc sulfite, and ammonium sulfite; hydrogensulfites such as sodium hydrogensulfite, potassium hydrogensulfite, calcium hydrogensulfite, and ammonium hydrogensulfite; pyrosulfites such as sodium pyrosulfite, potassium pyrosulfite, and ammonium pyrosulfite; dithionites such as sodium dithionite, potassium dithionite, ammonium dithionite, calcium dithionite, and zinc dithionite; trithionates such as potassium trithionate and sodium trithionate; tetrathionates such as potassium tetrathionate and sodium tetrathionate; thiosulfates such as sodium thiosulfate, potassium thiosulfate, and ammonium thiosulfate; nitrites such as sodium nitrite, potassium nitrite, calcium nitrite, and zinc nitrite; and the like. Among them, sulfites, hydrogensulfites, pyrosulfites, and dithionites are preferable, and sodium sulfite, sodium hydrogensulfite, potassium pyrosulfite, and sodium dithionite are more preferably used.

The oxidizing agent usable in the present invention includes chlorites such as sodium chlorite; hypochlorites such as sodium hypochlorite, potassium hypochlorite, and calcium hypochlorite; peroxides such as hydrogen peroxide, sodium peroxide, potassium peroxide, potassium permanganate, sodium peroxoborate, benzoyl peroxide, and lauroyl peroxide; and the like. Among them, hydrogen peroxide is preferably used.

The amount of the reducing agent or the oxidizing agent mentioned above used is 0.001 to 6 parts by weight, preferably from 0.005 to 3 parts by weight, more preferably from 0.01 to 2 parts by weight, based on 100 parts by weight of the α,β-unsaturated carboxylic acid. The amount of the reducing agent or the oxidizing agent used is 0.001 parts by weight or more, from the viewpoint of obtaining a water-absorbent resin having little discoloration even immediately after the preparation. In addition, the amount of the reducing agent or the oxidizing agent used is 6 parts by weight or less, from the viewpoint of obtaining the effect corresponding to the amount used, thereby being economically advantageous.

In the process of the present invention, the combination of the reducing agent or the oxidizing agent with the metal chelating agent to be added is not particularly limited. The combination of a sulfite, a hydrogensulfite, a pyrosulfite, a dithionite or a peroxide with a phosphoric acid-based metal chelating agent and/or an aminocarboxylic acid-based metal chelating agent is preferable, from the viewpoint of obtaining a water-absorbent resin having little discoloration even immediately after the preparation, and having suppressed discoloration even when subjected to a room temperature storage or even to a high-temperature, high-humidity storage for a long period of time. Among them, combinations of sodium sulfite, sodium hydrogensulfite, potassium pyrosulfite, sodium dithionite or hydrogen peroxide, with at least one member selected from the group consisting of diethylenetriaminepentaacetic acid, triethylenetetraminehexaacetic acid, trans-1,2-diaminocyclohexanetetraacetic acid, ethylenediaminetetraacetic acid, tripolyphosphoric acid, and salts thereof are more preferable, and combinations of sodium sulfite or sodium hydrogensulfite with at least one member selected from the group consisting of diethylenetriaminepentaacetic acid, triethylenetetraminehexaacetic acid, trans-1,2-diaminocyclohexanetetraacetic acid, and salts thereof are even more preferable.

Therefore, according to the present invention, there is provided a method for preventing discoloration of a water-absorbent resin made from an $\alpha,\beta$-unsaturated carboxylic acid as an essential monomer, wherein the method comprises preparing the water-absorbent resin by a process comprising allowing a metal chelating agent to be present at any step in the process in an amount of 0.001 to 6 parts by weight, based on 100 parts by weight of the $\alpha,\beta$-unsaturated carboxylic acid; and adding a reducing agent or an oxidizing agent thereto in an amount of 0.001 to 6 parts by weight, based on 100 parts by weight of the $\alpha,\beta$-unsaturated carboxylic acid before initiation of drying and/or during drying of a gelated product containing a water-absorbent resin obtained by polymerization.

In a case of a water-absorbent resin obtained by a process comprising adding a reducing agent or an oxidizing agent without adding a metal chelating agent, while Yellow Index immediately after the preparation is lower than a case where the reducing agent or the oxidizing agent is not added. Meanwhile, Yellow Index of such a resin increases with the passage of time at room temperature or moreover under high-temperature high-humidity conditions, which is the same as in the case where the reducing agent or the oxidizing agent is not added. On the other hand, the water-absorbent resin obtained by the process of the present invention comprising adding a reducing agent or an oxidizing agent and a metal chelating agent has very low Yellow Index immediately after the preparation, and a subsequent increase in Yellow Index with the passage of time is remarkably suppressed.

The water-absorbent resin made from an $\alpha,\beta$-unsaturated carboxylic acid as an essential monomer prepared in the present invention includes crosslinked products of acrylate polymers, crosslinked products of hydrolysates of starch-acrylate graft copolymers, crosslinked products of vinyl alcohol-acrylate copolymers, crosslinked products of maleic anhydride-grafted polyvinyl alcohol, crosslinked isobutylene-maleic anhydride copolymers, partially neutralized crosslinked products of polyacrylic acid, saponified products of vinyl acetate-acrylic ester copolymers, and the like. Among them, preferable are the crosslinked products of acrylate polymers which are capable of absorbing a large amount of water and retaining absorbed water in the molecule even when a certain load is applied.

The $\alpha,\beta$-unsaturated carboxylic acid includes, for instance, acrylic acid, methacrylic acid, maleic acid, maleic anhydride, fumaric acid and the like. These can be used alone or in admixture of two or more kinds. The $\alpha,\beta$-unsaturated carboxylic acid may be partially neutralized with an alkali metal or the like, and especially acrylic acid, methacrylic acid, and an alkali metal salt thereof, such as sodium or potassium are preferably used.

The above-mentioned $\alpha,\beta$-unsaturated carboxylic acid may be copolymerized with other monomers as occasion demands. Other monomers include, for instance, nonionic, hydrophilic group-containing monomers such as (meth)acrylamide ["(meth)acryl-" means "acryl-" and "methacryl-;" hereinafter referred to the same], N-substituted (meth)acrylamide, 2-hydroxyethyl (meth)acrylate, 2-hydroxypropyl (meth)acrylate, methoxypolyethylene glycol (meth)acrylate, and polyethylene glycol (meth)acrylate; unsaturated amino group-containing monomers such as N,N-dimethylaminoethyl (meth)acrylate, N,N-dimethylaminopropyl (meth)acrylate, N,N-dimethylaminopropyl (meth)acrylamide; sulfonic acid-based monomers such as vinylsulfonic acid, styrenesulfonic acid, 2-(meth)acrylamide-2-methylpropanesulfonic acid, 2-(meth)acryloylethanesulfonic acid and salts thereof; and the like.

The polymerization method of the water-absorbent resin according to the reversed phase suspension polymerization method will be exemplified hereinbelow.

In the reversed phase suspension polymerization method, the polymerization is carried out by using, for instance, a polymerization initiator in a state that an aqueous solution of the monomers is dispersed in an organic solvent in the presence of at least one of the surfactants and the polymeric protective colloids.

It is preferable that the concentration of the monomers in the above-mentioned aqueous solution of the monomers is from 25% by weight to a saturated concentration. In addition, the above-mentioned aqueous solution of the monomers may be added at once or may be added in divided portions in the polymerization reaction.

The above-mentioned organic solvent includes aliphatic hydrocarbon solvents such as n-pentane, n-hexane, n-heptane, and ligroin; alicyclic hydrocarbon solvents such as cyclopentane, methylcyclopentane, cyclohexane, and methylcyclohexane; aromatic hydrocarbon solvents such as benzene, toluene and xylene; and the like. Among them, n-heptane and cyclohexane are preferably used.

The amount of the organic solvent used is preferably from 50 to 600 parts by weight, more preferably from 100 to 550 parts by weight, based on 100 parts by weight of the total amount of the monomers, from the viewpoints of removing heat of polymerization, thereby making it easy to control the polymerization temperature.

The above-mentioned surfactant includes nonionic surfactants such as sorbitan fatty acid esters, monoglycerol fatty acid esters, polyglycerol fatty acid esters, sucrose fatty acid esters, polyoxyethylene hydrogenated castor oil, polyoxyethylene laurate hydrogenated castor oil, polyoxyethylene triisostearate hydrogenated castor oil, polyoxyethylene alkylphenyl ethers, polyoxyethylene lauryl ethers, and polyoxyethylene hexyldecyl ethers.

The above-mentioned polymeric protective colloid includes ethyl cellulose, hydroxyethyl cellulose, polyethylene oxide, polyethylene modified with maleic anhydride, polybutadiene modified with maleic anhydride, ethylene-propylene-diene terpolymers modified with maleic anhydride, and the like.

These nonionic surfactants and polymer protective colloids may be used in admixture of two or more kinds.

The nonionic surfactant and/or the polymeric protective colloids mentioned above can be used together with an anionic surfactant. The anionic surfactant includes salts of fatty acids, alkylbenzenesulfonates, alkyl methyl taurates, polyoxyethylene alkylphenyl ether sulfates, polyoxyethylene alkyl ether sulfonates and the like.

The amount of the surfactant and/or the polymeric protective colloid used is preferably from 0.1 to 5 parts by weight, more preferably from 0.2 to 3 parts by weight, based on 100 parts by weight of the total amount of the monomers, from the viewpoints of having satisfactory dispersion of the aqueous solution of monomers, obtaining an effect corresponding to the amount used, and being economically advantageous.

The above-mentioned water-absorbent resin can be prepared in a self-crosslinking reaction without using a crosslinking agent. Also, the resin can be crosslinked using an internal crosslinking agent having two or more polymerizable unsaturated groups or two or more reactive groups. The internal crosslinking agent includes a compound having two or more unsaturated ethylenic groups in one molecule, such as N,N'-methylenebis(meth)acrylamide, ethylene glycol di(meth)acrylate, diethylene glycol di(meth)acrylate, triethylene glycol di(meth)acrylate, trimethylolpropane di(meth)acrylate, trimethylolpropane tri(meth)acrylate, trimethylolpropane di(meth)allyl ether, and triallylamine; polyglycidyl ethers, such as (poly)ethylene glycol diglycidyl ether and glycerol triglycidyl ether; halogenated epoxy compounds, such as epichlorohydrin and epibromohydrin; and the like. One or more of these can be used upon considering the reactivity and water solubility in the polymerization system. It is preferable that the compound having two or more glycidyl groups in one molecule is used as the internal crosslinking agent.

The amount of the internal crosslinking agent used is preferably from 0.001 to 3 parts by weight, more preferably from 0.003 to 1 part by weight, even more preferably from 0.005 to 0.5 parts by weight, based on 100 parts by weight of the total amount of the above-mentioned monomers, from the viewpoints of suppressing the water-soluble nature of the resulting water-absorbent resin by an appropriate crosslinking, and showing a satisfactory water absorbency.

The polymerization initiator includes radical polymerization initiators such as potassium persulfate, sodium persulfate, ammonium persulfate, benzoyl peroxide, hydrogen peroxide, 1,1'-azobis(cyclohexane-1-carbonitrile), 2,2'-azobis(2-methyl-butyronitrile), 2,2'-azobisisobutyronitrile, 2,2'-azobis(2-amidinopropane)dihydrochloride, 2-cyano-2-propylazoformamide, dimethyl 2,2'-azobis(2-methylpropionate). The radical polymerization initiator as mentioned above may be used together with a sulfite or the like as a redox-system polymerization initiator.

It is desired that the amount of the polymerization initiator used is from 0.005 to 1 mol per 100 mol of the total amount of the above-mentioned monomers, from the viewpoints of shortening the time for the polymerization reaction, preventing an unreasonable polymerization reaction, and facilitating the control of the polymerization reaction.

The surfactant and/or the polymeric protective colloid mentioned above is dissolved in an organic solvent, and the mixture of the above-mentioned aqueous solution of the monomers, the polymerization initiator and the like are added to the above-mentioned organic solution. The mixture is heated while stirring, and subjected to reversed phase suspension polymerization in a water-in-oil system. The reaction temperature of the above-mentioned polymerization reaction differs depending upon the kinds of the polymerization initiator and the monomers used, or the concentration of the aqueous solution of the monomers. The reaction temperature is preferably from 20° to 110° C., more preferably from 40° to 80° C., from the viewpoints of rapidly progressing the polymerization, shortening the polymerization time, being economically favorable, making the removal of the heat of reaction easier, and smoothly carrying out the reaction. The reaction time is usually from 0.5 to 4 hours.

The resulting water-absorbent resin may be subjected to surface-crosslinking by treating the water-absorbent resin with a crosslinking agent having two or more functional groups having reactivity with carboxyl groups. The surface-crosslinking agent includes those capable of reacting with carboxyl groups in the water-absorbent resin, for instance, epoxy compounds such as (poly)ethylene glycol diglycidyl ether, (poly)propylene glycol diglycidyl ether, (poly)glycerol polyglycidyl ethers, and glycidol; halogenated epoxy compounds such as epichlorohydrin, epibromohydrin, α-methyl-epichlorohydrin; polyhydric alcohol compounds such as (poly)ethylene glycol, (poly)propylene glycol, (poly)glycerol, diols, pentanediols, hexanediols, trimethylolpropane, diethanolamine, and triethanolamine; and the like. Among them, the epoxy compound is more preferably used. These surface-crosslinking agents can be used alone or in combination of two or more kinds.

The amount of the surface-crosslinking agent used is preferably from 0.01 to 5 parts by weight, more preferably from 0.02 to 4 parts by weight, even more preferably from 0.03 to 3 parts by weight, based on 100 parts by weight of the total amount of the above-mentioned monomer, from the viewpoints of obtaining satisfactory gel strength and water absorbency during water absorption of the water-absorbent resin.

The method of adding the above-mentioned surface-crosslinking agent is not particularly limited. The method includes, for instance, a method comprising adding the above-mentioned surface-crosslinking agent to a water-absorbent resin dispersed in an organic solvent; a method comprising spraying the above-mentioned surface-crosslinking agent to a water-absorbent resin with a spray or the like while stirring; and the like. The timing of the addition for the surface-crosslinking agent includes the stage of the water-containing gelated product after the polymerization; the stage of the water-containing particles during drying; the stage after drying; and the like. Among them, a method comprising adding the surface-crosslinking agent to a water-absorbent resin dispersed in an organic solvent at the stage of the water-containing gelated product after the polymerization, and a method comprising spraying with a spray or the like at the stage of the water-containing particles during drying are preferable.

The embodiment of adding the surface-crosslinking agent is not particularly limited. In order that the surface-crosslinking agent is homogeneously added to the water-absorbent resin, it is preferable that the surface-crosslinking agent is dissolved in a hydrophilic solvent such as water before addition.

The water-absorbent resin can be prepared by drying the water-absorbent resin obtained by the polymerization method mentioned above, and removing water and an organic solvent therefrom. The resulting water-absorbent resin may be classified with sieves or the like as occasion demands.

In a case where the resulting water-absorbent resin is used in the form of an absorbent and an absorbent article, Yellow Index is preferably 12 or less, more preferably 10 or less, after the water-absorbent resin is allowed to stand at 50° C. under a 90% relative humidity for 20 days. Furthermore, the difference between Yellow Index of the water-absorbent resin after being allowed to stand at 50° C. under 90% relative humidity for 20 days and Yellow Index of the water-absorbent resin before being allowed to stand is preferably 2 or less, more preferably 1 or less. Here, Yellow Index in the present invention refers to a value determined by the measurement method described later.

In the present invention, an absorbent and an absorbent article can be produced using the water-absorbent resin obtained by the above-mentioned preparation process. The absorbent comprises a water-absorbent resin and a hydrophilic fiber. The usable hydrophilic fiber includes cellulose fibers, artificial cellulose fibers and the like, without being particularly limited thereto. The hydrophilic fiber may contain a synthetic fiber. The proportion of the water-absorbent resin and the hydrophilic fiber is not particularly limited. In addition, the constitution of the absorbent includes, for instance, a mixing structure in which a water-absorbent resin and a hydrophilic fiber are homogeneously blended; a sandwich structure in which a water-absorbent resin is spread between layered hydrophilic fibers; and the like, without being particularly limited thereto.

The absorbent article can be produced by, for instance, putting the above-mentioned absorbent between a liquid-permeable sheet and a liquid-impermeable sheet. The liquid-permeable sheet includes porous sheets or nonwoven fabrics made of polyethylene, polypropylene, or a polyester, and the like, and the liquid-impermeable sheet includes synthetic resin films made of polyethylene, polypropylene or polyvinyl chloride, and the like, without being limited thereto.

The absorbent article using the water-absorbent resin of the present invention is preferably, for instance, a hygienic material such as paper diaper, sanitary napkin or incontinence pad; a urine-absorbing material for pets, without being particularly limited thereto. Besides, there can be used, for instance, for materials for civil engineering and construction such as packing materials; food freshness retaining materials such as drip absorbents and keeping cool agents; horticultural articles such as water-retaining materials for soils; and the like.

The present invention will be explained hereinbelow by means of Examples and Comparative Examples, without intending to limit the present invention only to these Examples.

Example 1

Five-hundred milliliters of n-heptane was added to a 1000-ml five-necked cylindrical round bottomed flask equipped with a stirrer, a reflux condenser, a dropping funnel, a thermometer and a nitrogen gas inlet tube. Thereto was added 0.92 g of sucrose fatty acid ester (surfactant: S-370, manufactured by MITSUBISHI CHEMICAL CORPORATION) having an HLB of 3.0 and dispersed. The temperature of the dispersion was raised to dissolve the surfactant, and thereafter cooled to 55° C.

Separately from the above, 92 g of a 80% by weight aqueous solution of acrylic acid was added to a 500-ml Erlenmeyer flask. Thereto was added dropwise 102.2 g of a 30% by weight aqueous sodium hydroxide solution while externally cooling, to neutralize 75% by mol of acrylic acid, to give a partially neutralized salt of acrylic acid. Further, 50.2 g of water, 0.11 g of a polymerization initiator potassium persulfate, and 9.2 mg of a crosslinking agent ethylene glycol diglycidyl ether were added thereto, to give an aqueous solution of a monomer for a first step polymerization.

The entire amount of this aqueous solution of the monomer for a first step polymerization was added to the above-mentioned five-necked cylindrical round bottomed flask under stirring and dispersed. After the internal of the system was sufficiently replaced with nitrogen, the temperature of the mixture was raised, and the polymerization reaction was carried out for 1 hour while keeping its bath temperature at 70° C. Thereafter, the polymerization slurry was cooled to room temperature.

Further, 119.1 g of a 80% by weight aqueous solution of acrylic acid was added to a separate 500-ml Erlenmeyer flask. Thereto was added dropwise 132.2 g of a 30% by weight aqueous sodium hydroxide solution while cooling, to neutralize 75% by mol of acrylic acid. Further, 27.4 g of water, 0.14 g of potassium persulfate, and 35.7 mg of ethylene glycol diglycidyl ether were added thereto, to give an aqueous solution of a monomer for a second step polymerization. The aqueous solution was cooled in an ice water bath.

The entire amount of this aqueous solution of the monomer for a second step polymerization was added to the above-mentioned polymerization slurry. After the internal of the system was again sufficiently replaced with nitrogen, the temperature of the mixture was raised, and the second-step polymerization reaction was carried out for 2 hours while keeping its bath temperature at 70° C. After the termination of the polymerization, 3.52 g of a 3% by weight aqueous sodium sulfite solution was added to a water-containing gelated product dispersed in n-heptane, and the mixture was stirred for 30 minutes. Thereafter, 5.28 g of a 40% by weight aqueous solution of pentasodium diethylenetriaminepentaacetate was added thereto under stirring. Subsequently, water of the water-containing gelated product was removed to the external of the system by azeotropic dehydration. To the resulting gelated product was added 8.44 g of a 2% by weight aqueous solution of ethylene glycol diglycidyl ether, and water and n-heptane were further removed from the mixture by distillation, and the residue was dried, to give 215.5 g of a water-absorbent resin.

Example 2

The same procedures as in Example 1 were carried out except that the amount of the 40% by weight aqueous solution of pentasodium diethylenetriaminepentaacetate in Example 1 was changed to 0.528 g, to give 213.1 g of a water-absorbent resin.

Example 3

The same procedures as in Example 1 were carried out except that the amount of the 40% by weight aqueous solution of pentasodium diethylenetriaminepentaacetate in Example 1 was changed to 0.264 g, to give 212.9 g of a water-absorbent resin.

Example 4

Five-hundred milliliters of n-heptane was added to a 1000-ml five-necked cylindrical round bottomed flask equipped with a stirrer, a reflux condenser, a dropping funnel, a thermometer and a nitrogen gas inlet tube. Thereto was added 1.38 g of decaglycerol pentastearate (surfactant: SUNSOFT Q-185S, manufactured by Taiyo Kagaku Co., Ltd.) having an HLB of 5.0 and dispersed. The temperature of the dispersion was raised to dissolve the surfactant, and thereafter cooled to 55° C.

Separately from the above, 92 g of a 80% by weight aqueous solution of acrylic acid was added to a 500-ml Erlenmeyer flask. Thereto was added dropwise 102.2 g of a 30% by weight aqueous sodium hydroxide solution while externally cooling, to neutralize 75% by mol of acrylic acid, to give a partially neutralized salt of acrylic acid. Further, 50.2 g of water, 0.11 g of a polymerization initiator potassium persulfate, and 18.4 mg of a crosslinking agent ethylene glycol diglycidyl ether were added thereto, to give an aqueous solution of a monomer for the polymerization.

The entire amount of this aqueous solution of the monomer for the polymerization was added to the above-mentioned five-necked cylindrical round bottomed flask under stirring and dispersed. After the internal of the system was sufficiently replaced with nitrogen, the temperature of the mixture was raised, and the polymerization reaction was carried out for 1 hour while keeping its bath temperature at 70° C. After the termination of the polymerization, 3.07 g of a 3% by weight aqueous sodium hydrogensulfite solution was added thereto, and the mixture was stirred for 30 minutes. Thereafter, 0.66 g of a 14% by weight aqueous solution of tetrasodium trans-1, 2-diaminocyclohexanetetraacetate was added to a water-containing gelated product dispersed in n-heptane under stirring.

Subsequently, water of the water-containing gelated product was removed to the external of the system by azeotropic dehydration. To the resulting gelated product was added 4.14 g of a 2% by weight aqueous solution of ethylene glycol diglycidyl ether, and water and n-heptane were further removed from the mixture by distillation, and the residue was dried, to give 92.3 g of a water-absorbent resin.

Example 5

The same procedures as in Example 4 were carried out except that 3.07 g of the 3% by weight aqueous sodium hydrogensulfite solution in Example 4 was changed to 1.53 g of a 3% by weight aqueous sodium dithionite solution, and that 0.66 g of the 14% by weight aqueous solution of tetrasodium trans-1,2-diaminocyclohexanetetraacetate in Example 4 was changed to 0.24 g of a 38% by weight aqueous solution of tetrasodium ethylenediaminetetraacetate, to give 92.1 g of a water-absorbent resin.

Example 6

Five-hundred milliliters of n-heptane was added to a 1000-ml five-necked cylindrical round bottomed flask equipped with a stirrer, a reflux condenser, a dropping funnel, a thermometer and a nitrogen gas inlet tube. Thereto was added 0.92 g of sucrose fatty acid ester (surfactant: S-370, manufactured by MITSUBISHI CHEMICAL CORPORATION) having an HLB of 3.0 and dispersed. The temperature of the dispersion was raised to dissolve the surfactant, and thereafter cooled to 55° C.

Separately from the above, 92 g of a 80% by weight aqueous solution of acrylic acid was added to a 500-ml Erlenmeyer flask. Thereto was added dropwise 102.2 g of a 30% by weight aqueous sodium hydroxide solution while externally cooling, to neutralize 75% by mol of acrylic acid, to give a partially neutralized salt of acrylic acid. Further, 50.2 g of water, 0.11 g of a polymerization initiator potassium persulfate, and 9.2 mg of a crosslinking agent ethylene glycol diglycidyl ether were added thereto, to give an aqueous solution of monomers for the polymerization.

The entire amount of this aqueous solution of the monomers for the polymerization was added to the above-mentioned five-necked cylindrical round bottomed flask under stirring and dispersed. After the internal of the system was sufficiently replaced with nitrogen, the temperature of the mixture was raised, and the polymerization reaction was carried out for 1 hour while keeping its bath temperature at 70° C. After the termination of the polymerization, water of the water-containing gelated product was removed to the external of the system by azeotropic dehydration. To the resulting gelated product were added 3.07 g of a 3% by weight aqueous solution of potassium pyrosulfite and 4.14 g of a 2% by weight aqueous solution of ethylene glycol diglycidyl ether. Water was removed again together with n-heptane by distillation, and the residue was dried. Thereafter, 0.46 g of a powder triethylenetetraminehexaacetic acid (87% by weight of the entire particles thereof having sizes of 100 μm or less) was added to the residue under stirring, and the mixture was further dried, to give 93.5 g of a water-absorbent resin.

Example 7

The same procedures as in Example 6 were carried out except that 3.07 g of the 3% by weight aqueous solution of potassium pyrosulfite in Example 6 was changed to 1.53 g of a 3% by weight aqueous sodium sulfite solution, and that triethylenetetraminehexaacetic acid was not added, to give 92.2 g of a water-absorbent resin. The entire amount of the above-mentioned water-absorbent resin and 0.92 g of a powder disodium diethylenetriaminepentaacetate (85% by weight of the entire particles having particle sizes of 100 μm or less) were added into a polyethylene bag, and the mixture was sufficiently mixed, to give 93.1 g of a water-absorbent resin.

Example 8

Five-hundred milliliters of n-heptane was added to a 1000-ml five-necked cylindrical round bottomed flask equipped with a stirrer, a reflux condenser, a dropping funnel, a thermometer and a nitrogen gas inlet tube. Thereto was added 0.92 g of sorbitan monostearate (surfactant: Nonion SP-60R, manufactured by NOF Corporation) having an HLB of 4.7 and dispersed. The temperature of the dispersion was raised to dissolve the surfactant, and thereafter cooled to 50° C.

Separately from the above, 92 g of a 80% by weight aqueous solution of acrylic acid was added to a 500-ml Erlenmeyer flask. Thereto was added dropwise 102.2 g of a 30% by weight aqueous sodium hydroxide solution while externally cooling, to neutralize 75% by mol of acrylic acid, to give a partially neutralized salt of acrylic acid. Further, 20.8 g of water, 0.11 g of a polymerization initiator potassium persulfate, and 23.0 mg of a crosslinking agent N,N'-methylenebisacrylamide were added thereto. To the mixture was added 0.092 g of sodium tripolyphosphate, to give an aqueous solution of a monomer for the polymerization.

The entire amount of this aqueous solution of the monomer for the polymerization was added to the above-mentioned five-necked cylindrical round bottomed flask under stirring and dispersed. After the internal of the system was sufficiently replaced with nitrogen, the temperature of the mixture was raised, and the polymerization reaction was carried out for 2 hours while keeping its bath temperature at 70° C. After the termination of the polymerization, 0.153 g of a 3% by weight aqueous hydrogen peroxide solution was added thereto, and the mixture was stirred for 30 minutes. Subsequently, water of the water-containing gelated product was removed to the external of the system by azeotropic dehydration. To the resulting gelated product was added 4.60 g of a 2% by weight aqueous solution of ethylene glycol diglycidyl ether, and water and n-heptane were further removed from the mixture by distillation, and the residue was dried, to give 94.2 g of a water-absorbent resin.

Comparative Example 1

The same procedures as in Example 1 were carried out except that the aqueous sodium sulfite solution and the aqueous solution of pentasodium diethylenetriaminepentaacetate in Example 1 were not used, to give 214.5 g of a water-absorbent resin.

Comparative Example 2

The same procedures as in Example 1 were carried out except that the aqueous solution of pentasodium diethylenetriaminepentaacetate in Example 1 was not used, to give 215.1 g of a water-absorbent resin.

Comparative Example 3

The same procedures as in Example 1 were carried out except that the aqueous sodium sulfite solution in Example 1 was not used, to give 214.7 g of a water-absorbent resin.

Comparative Example 4

The same procedures as in Example 6 were carried out except that triethylenetetraminehexaacetic acid in Example 6 was not used, to give 92.9 g of a water-absorbent resin.

Comparative Example 5

The same procedures as in Example 8 were carried out except that sodium tripolyphosphate in Example 8 was not used, to give 93.8 g of a water-absorbent resin.

Comparative Example 6

The same procedures as in Example 8 were carried out except that hydrogen peroxide in Example 8 was not used, to give 94.0 g of a water-absorbent resin.

The discoloration test of the water-absorbent resins obtained in Examples and Comparative Examples mentioned above, and the discoloration test of the absorbent articles prepared using the water-absorbent resins were carried out in accordance with the following methods.

(1) Discoloration Test of Water-Absorbent Resins

Into a polypropylene vessel having an inner diameter of 3 cm and a depth of 1 cm was evenly placed 2.0 g of a water-absorbent resin. This vessel was allowed to stand for 20 days in a bench-type thermohygrostat set at a temperature of 50°±2° C. and relative humidity of 90±2% RH. After allowing to stand, the vessel was taken out from the thermohygrostat, and allowed to stand for some time to cool to room temperature. The entire amount of the water-absorbent resin in the vessel was added to a glass measuring vessel having an inner diameter of 3 cm, and Yellow Index of the water-absorbent resin was determined with a double beam-type spectrocolorimeter Z-1001DP (manufactured by Nippon Denshoku Kogyo Industries, Co., Ltd.), in which X, Y and Z, tristimulus values of the spectrocolorimeter are corrected with a standard white board. Yellow Index was calculated by the following equations from X, Y and Z (tristimulus values) of the resulting water-absorbent resin. Similarly, Yellow Index of the water-absorbent resin before the test of allowing to stand in the bench-type thermohygrostat for 20 days was obtained. The above-mentioned determinations were taken thrice, and an averaged value was obtained.

$$\text{Yellow Index} = 100(1.28X - 1.06Z)/Y$$

(2) Discoloration Test of Absorbent Article

A blend of 5 g of a water-absorbent resin and 5 g of a disintegrated pulp was formed on a tissue paper of 20×12 cm by air-blow molding. A tissue paper of the same size was overlaid thereto, and thereafter a 145 kPa load was applied thereto for 30 seconds, to give an absorbent. This absorbent was inserted between a polyethylene air-through-type nonwoven fabric having a weighing capacity of 20 g/cm$^2$ placed on top and a liquid-impermeable polyethylene sheet at bottom, to give an absorbent article. This absorbent article was allowed to stand for 50 days in a bench-type thermohygrostat set at a temperature of 50°±2° C. and relative humidity of 90±2% RH. After allowing to stand, the discoloration of the water-absorbent resin in the absorbent article was visually observed, and evaluated according to the following criteria.

[Evaluation Criteria]

A: Inner water-absorbent resin does not discolor when observed while removing the nonwoven fabric and unweaving the absorbent.

B: Although discoloration due to the water-absorbent resin is not found when observed from the top of the nonwoven fabric, discoloration is found in a part of the water-absorbent resin when the nonwoven fabric is removed and the absorbent is unweaved.

C: Discoloration due to the water-absorbent resin is found when observed from the top of the nonwoven fabric.

The metal chelating agent, and the oxidizing agent or reducing agent used in Examples and Comparative Examples mentioned above are shown in Table 1. The amount inside the parenthesis in Table 1 is an amount based on 100 parts by weight of acrylic acid.

TABLE 1

|  | Metal Chelating Agent (parts by weight) | Reducing Agent or Oxidizing Agent (parts by weight) |
|---|---|---|
| Ex. 1 | Pentasodium Diethylenetriaminepentaacetate (1.25) | Sodium Sulfite (0.0625) |
| Ex. 2 | Pentasodium Diethylenetriaminepentaacetate (0.125) | Sodium Sulfite (0.0625) |
| Ex. 3 | Pentasodium Diethylenetriaminepentaacetate (0.0625) | Sodium Sulfite (0.0625) |
| Ex. 4 | Tetrasodium trans-1,2-Diaminocyclohexanetetraacetate (0.125) | Sodium Hydrogensulfite (0.125) |
| Ex. 5 | Tetrasodium Ethylenediaminetetraacetate (0.124) | Sodium Dithionite (0.0624) |
| Ex. 6 | Triethylenetetraminehexaacetic acid (0.625) | Potassium Pyrosulfite (0.125) |
| Ex. 7 | Disodium Diethylenetriaminepentaacetate (1.25) | Sodium Sulfite (0.0624) |
| Ex. 8 | Sodium Tripolyphosphate (0.125) | Hydrogen Peroxide (0.00624) |
| Comp. Ex. 1 | (Not Added) | (Not Added) |
| Comp. Ex. 2 | (Not Added) | Sodium Sulfite (0.0625) |
| Comp. Ex. 3 | Pentasodium Diethylenetriaminepentaacetate (1.25) | (Not Added) |
| Comp. Ex. 4 | (Not Added) | Potassium Pyrosulfite (0.125) |
| Comp. Ex. 5 | (Not Added) | Hydrogen Peroxide (0.00624) |
| Comp. Ex. 6 | Sodium Tripolyphosphate (0.125) | (Not Added) |

In addition, the results for the discoloration test of the water-absorbent resins obtained in Examples and Comparative Examples mentioned above, and the discoloration test of the absorbent articles prepared using the water-absorbent resins are shown in Table 2.

TABLE 2

| | Results for Discoloration Test | | | |
|---|---|---|---|---|
| | Water-Absorbent Resin | | | Absorbent |
| | Yellow Index Before Test ($YI_a$) | Yellow Index After Test ($YI_b$) | Difference in Yellow Index ($YI_b - YI_a$) | Article Visual Evaluation |
| Ex. 1 | 6.8 | 7.0 | 0.2 | A |
| Ex. 2 | 7.1 | 7.6 | 0.5 | A |
| Ex. 3 | 7.4 | 8.2 | 0.8 | A |
| Ex. 4 | 7.2 | 7.8 | 0.6 | A |
| Ex. 5 | 7.3 | 8.7 | 1.4 | A |
| Ex. 6 | 6.9 | 7.3 | 0.4 | A |
| Ex. 7 | 7.2 | 8.1 | 0.9 | A |
| Ex. 8 | 7.5 | 9.5 | 2.0 | A |
| Comp. Ex. 1 | 10.4 | 21.1 | 10.7 | C |
| Comp. Ex. 2 | 7.7 | 24.0 | 16.3 | C |

TABLE 2-continued

Results for Discoloration Test

| | Water-Absorbent Resin | | | Absorbent Article Visual Evaluation |
|---|---|---|---|---|
| | Yellow Index Before Test ($YI_a$) | Yellow Index After Test ($YI_b$) | Difference in Yellow Index ($YI_b-YI_a$) | |
| Comp. Ex. 3 | 9.7 | 13.3 | 3.6 | B |
| Comp. Ex. 4 | 6.8 | 25.1 | 18.3 | C |
| Comp. Ex. 5 | 7.5 | 26.3 | 18.8 | C |
| Comp. Ex. 6 | 10.2 | 17.3 | 7.1 | C |

It can be seen from the results for the discoloration test of the water-absorbent resin of Table 2 that the water-absorbent resins obtained in Examples have low Yellow Index, and little change in Yellow Index even when subjected to high-temperature, high-humidity storage, so that the discoloration is suppressed. The water-absorbent resins to which the reducing agent or oxidizing agent is not added obtained in Comparative Examples 1, 3 and 6 have high Yellow Index before the test as compared to the water-absorbent resin obtained in Examples. The water-absorbent resins to which the reducing agent or oxidizing agent is added but not a metal chelating agent obtained in Comparative Examples 2, 4 and 5 have low Yellow Index immediately after the preparation, but have a large change in Yellow Index when subjected to high-temperature, high-humidity storage, and more likely to discolor. Further, it can be seen from the results for the discoloration test by visual observation of the absorbent articles that the discoloration in the water-absorbent resin after being subjecting to a high-temperature, high-humidity storage is not found in the absorbent articles obtained in Examples, while the discoloration in the water-absorbent resin after being subjecting to high-temperature, high-humidity storage is found in the absorbent articles obtained in Comparative Examples.

INDUSTRIAL APPLICABILITY

According to the present invention, there can be prepared a water-absorbent resin having no discoloration immediately after the preparation, and having suppressed discoloration even when subjected to a room temperature storage or high-temperature, high-humidity storage for a long period of time. Therefore, an absorbent and an absorbent article using the water-absorbent resin obtained by the process of the present invention maintain excellent commercial values.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A process for preparing a water-absorbent resin, wherein said process comprises:
   a) polymerizing to completion an α,β-unsaturated carboxylic acid monomer to produce a polymerized water-containing gelated product;
   b) adding a metal chelating agent at any step in the preparation of the water-absorbent resin, wherein said metal chelating agent is added in an amount of 0.001 to 6 parts by weight, based on 100 parts by weight of the α,β-unsaturated carboxylic acid;
   c) adding a reducing agent or an oxidizing agent to the polymerized water-containing gelated product in an amount of 0.001 to 2 parts by weight, based on 100 parts by weight of the α,β-unsaturated carboxylic acid; and
   d) drying the gelated product thereby yielding a polymerized water-absorbent resin having greater discoloration resistance than a polymerized water-absorbent resin having no reducing or oxidizing agent and no metal chelating agent added thereto.

2. The process for preparing a water-absorbent resin according to claim 1, wherein the reducing agent is a sulfite, a hydrogensulfite, a dithionite or a pyrosulfite.

3. The process for preparing a water-absorbent resin according to claim 1, wherein the oxidizing agent is hydrogen peroxide.

4. The process for preparing a water-absorbent resin according to claim 1, wherein the metal chelating agent is at least one member selected from the group consisting of diethylenetriaminepentaacetic acid, triethylenetetraminehexaacetic acid, trans-1,2-diaminocyclohexanetetraacetic acid, ethylenediaminetetraacetic acid, tripolyphosphoric acid, and salts thereof.

5. A water-absorbent resin obtained by the process of any one of claims 1 to 4, wherein the water-absorbent resin has Yellow Index of 12 or less, after allowing to stand at 50° C. and 90% relative humidity for 20 days.

6. An absorbent comprising a water-absorbent resin obtained by the process of any one of claims 1 to 4, and a hydrophilic fiber.

7. An absorbent article comprising the absorbent of claim 6, wherein the absorbent is kept between a liquid-permeable sheet and a liquid-impermeable sheet.

8. A process for preparing a water-absorbent resin, wherein said process comprises, in the following order:
   a) polymerizing to completion an α,β-unsaturated carboxylic acid monomer to produce a polymerized water-containing gelated product;
   b) adding a metal chelating agent at any step in the preparation of the water-absorbent resin, wherein said metal chelating agent is added in an amount of 0.001 to 6 parts by weight, based on 100 parts by weight of the α,β-unsaturated carboxylic acid;
   c) adding an oxidizing agent to the polymerized water-containing gelated product in an amount of 0.001 to 2 parts by weight, based on 100 parts by weight of the α,β-unsaturated carboxylic acid; and
   d) drying the gelated product thereby yielding a polymerized water-absorbent resin having greater discoloration resistance than a polymerized water-absorbent resin having no oxidizing agent and no metal chelating agent added thereto.

9. The process for preparing a water-absorbent resin according to claim 1, wherein the amount of the reducing agent or oxidizing agent added in step c) is 0.01 to 2 parts by weight, based on 100 parts by weight of the α,β-unsaturated carboxylic acid.

10. The process for preparing a water-absorbent resin according to claim 8, wherein the amount of the oxidizing agent added in step c) is 0.01 to 2 parts by weight, based on 100 parts by weight of the α,β-unsaturated carboxylic acid.

* * * * *